United States Patent [19]

Gill

[11] Patent Number: 5,402,189
[45] Date of Patent: Mar. 28, 1995

[54] SIDE SHIELD FOR EYEGLASSES AND METHOD OF MAKING THE SAME

[76] Inventor: Vicki L. Gill, 5022 Syndt Rd., Evergreen, Colo. 80439

[21] Appl. No.: 183,662

[22] Filed: Jan. 19, 1994

[51] Int. Cl.6 ............................................. G02C 7/10
[52] U.S. Cl. ........................................ 351/44; 2/13; 2/449
[58] Field of Search ................ 351/44, 122, 121, 123, 351/111, 41; 2/13, 449

[56] References Cited

U.S. PATENT DOCUMENTS

| | | | |
|---|---|---|---|
| 730,192 | 12/1901 | Moritz. | |
| 893,972 | 11/1907 | Bayless. | |
| 1,706,682 | 5/1928 | Takacs. | |
| 2,840,821 | 3/1956 | Gay, Jr. et al. | 2/13 |
| 2,900,639 | 8/1959 | Lindstrom | 2/13 |
| 3,721,490 | 5/1971 | Prince | 351/47 |
| 4,726,075 | 12/1986 | Hinrichs | 2/13 |
| 4,751,746 | 12/1986 | Rustin | 2/13 |

*Primary Examiner*—William L. Sikes
*Assistant Examiner*—Hung Xuan Dang
*Attorney, Agent, or Firm*—John E. Reilly

[57] ABSTRACT

A side shield for eyeglasses includes a metal foil shape-retentive member sandwiched between a neoprene base layer and an ornamental fabric cover layer. The shape-retentive member includes first and second arcuate lobe ends connected by a reduced width medial neck portion. Two pair of slits formed through the base and cover layers on opposite sides of the medial neck portion allows the shield to be slipped onto a temple region of an eyeglass earbow, without contact between the shape-retentive member and the earbow, and thereafter deformed to a custom configuration by a user to block peripheral light and wind. In a method of making the side shields, a plurality of preformed shape-retentive members are laminated to a neoprene base sheet. A fabric cover sheet is then laminated in overlying relation to the shape-retentive members and the base sheet to form a three layer laminate sheet. Specially configured dies or other cutting techniques are then used to cut mirror image left and right hand side shields from the laminate sheet.

21 Claims, 1 Drawing Sheet

SIDE SHIELD FOR EYEGLASSES AND METHOD OF MAKING THE SAME

BACKGROUND OF THE INVENTION

1. Field Of The Invention

This invention relates to side shields for eyeglasses and more particularly relates to an improved side shield adapted to slip on temple regions of eyeglass earbows for blocking peripheral light and wind, and to a method of making the improved side shields.

The eyes of many individuals are sensitive to light and to wind. Exposure to bright light, particularly in the ultraviolet region of the spectrum, is known to cause eye damage and long term repeated exposure is believed to contribute to the formation of cataracts in older individuals. Additionally, wind exposure tends to dry the natural lubricating tears, causing irritation. Wind born irritants such as dust and pollen affect some individuals with severity, including particularly contact lens wearers.

2. Description Of The Prior Art

Conventional sunglasses alleviate the aforementioned problems to some degree. However, such conventional sunglasses still expose the eyes of a wearer to peripheral light and wind entering from adjacent the temple region of the glasses. In order to overcome this problem, the prior art has proposed the use of so-called side shields comprising small generally triangular members adapted for attachment to the temple regions of the earbows of the eyeglasses. When installed in pairs on each earbow of a pair of eyeglasses, the prior art side shields substantially block peripheral light and wind from the eyes of a user. One type of conventional side shield includes a slotted portion for slip-on securement to the temple regions of earbows of the eyeglasses. Another prior art type of side shield for eyeglasses includes a fastening clip for securing the shield to the glasses.

The field of eyeglasses generally, and particularly the field of side shields is relatively crowded, and various prior art side shields are disclosed in several U.S. patents. For example, U.S. Pat. No. 730,192 to G. Morritz discloses an eyeglass side shield which is made up of laminations of cloth and metal. U.S. Pat. No. 4,751,746 to R. J. Rustin discloses a side shield which is composed of an insulated cloth material but is concerned as much with protection of the ears as to serve as an eyeglass side shield. U.S. Pat. No. 893,972 to W. C. Bayless discloses a shield which can be formed of leather, rubber, cloth or other suitable material but is attached directly to the frame and not to the temples of the eyeglasses. A similar approach is taken in U.S. Pat. No. 4,726,075 to M. T. Hinrichs in which the shield can be composed of leather, cloth, vinyl or the like. U.S. Pat. No. 3,721,490 to J. M. Prince discloses a side shield composed of transparent plastic which is clipped onto the temple region of an eyeglasses earbow. U.S. Pat. No. 2,900,636 to E. P. Lindstrom discloses a somewhat different type of a clip arrangement for a side shield, as also does U.S. Pat. No. 2,840,821 to F. G. Gay, Jr. et al. U.S. Pat. No. 1,706,682 to J. Takacs discloses a side shield made up of an oblong disk having an opening and notch to facilitate slipping onto the temples of the eyeglasses. The disk can be composed of various different materials including cardboard or rubber and is of a configuration such that the sides of the disk taper or converge rearwardly away from the front frame of the eyeglasses. Takacs does not suggest laminating different materials together to form the disk.

One side shield for eyeglasses available on the market under the brand name DOCTOR'S EYEWEAR ACCESSORIES includes a shape-retentive member in the form of a sheet metal insert loosely captured in a vinyl envelope such that a user may plastically deform the shield for a custom fit. This shield also includes a central slotted portion to allow removable slip on securement of the shield to the temple region of an eyeglasses earbow. However, this particular shield poses a safety hazard in that the relatively stiff and rigid metal insert might function as a knife in the event of a fall or other accident to severely injure the face and/or eyes of a user. The preformed securement slot and the non-elastic nature of the vinyl envelope make the shield suitable for use with only a narrow range of earbow dimensions. Additionally, the relatively great mass of the metal insert acts to transfer heat from the face of the user to ambient, thus making the shield unsuitable for cold weather use.

The various prior art side shields also pose the potential for marring eyeglasses and for irritating the skin of a wearer, particularly if deformed for the best possible fit, due to the rough and coarse materials used in their construction.

Finally, the prior art side shields present an unattractive appearance, thus discouraging use by fashion conscious individuals.

SUMMARY OF THE INVENTION

Accordingly, it is an object of the present invention to provide a novel and improved side shield for eyeglasses including pliable and shape-retentive characteristics allowing user deformation to mold the shield close to the edge of any size or shape of eyeglasses for an optimal custom fit without posing a safety hazard.

Another object of the present invention is to provide a novel and improved side shield for eyeglasses which provides a soft non-irritating and non-marring surface adjacent the face and eyeglasses of a user.

A further object of the present invention is to provide a novel and improved side shield for eyeglasses which provides an aesthetically pleasing appearance.

Still another object of the present invention is to provide a novel and improved side shield for eyeglasses adapted for removable securement to temple regions of a wide variety of different eyeglasses earbows without marring the eyeglasses.

A still further object of the present invention is to provide a novel and improved side shield for eyeglasses which provides thermal insulation in addition to blocking peripheral light and wind.

Yet another object of the present invention is to provide a novel and improved economical method of making side shields for eyeglasses by cutting left and right hand shields from a laminate sheet.

In order to achieve these and other objects of the invention, the present invention provides a side shield for eyeglasses which includes a plastically deformable shape-retentive member sandwiched between flexible base and cover layers. The shape-retentive member preferably has a thickness less than a thickness of at least one of the base and cover layers. More specifically, the base layer is formed from neoprene and the cover layer is formed from an ornamental fabric. The shape-retentive member is preferably formed from a pliable thin metal foil and includes first and second enlarged arcuate lobe ends separated by a reduced width medial neck portion. Two pairs of slits extending through the base and cover layers and disposed on opposite sides of the medial neck portion allow the shield to be slipped onto the temple region of an eyeglass earbow without potentially marring contact between the earbow and the shape-retentive member. A user may thereafter manually deform the shield to a desired custom configuration to block peripheral light and wind, with the soft and thermally insulating neoprene layer disposed adjacent the user's face and the eyeglasses.

In a method of making the side shields according to the present invention, a plurality of preformed shape-retentive members are initially laminated to a neoprene base sheet. A fabric cover sheet is then laminated in overlying relation to the base sheet and shape-retentive members, forming a three-layer laminate. Two pairs of slots are formed through each side shield flanking opposite sides of the shape-retentive members in order to facilitate attachment to the temple regions of the earbows of a pair of eyeglasses by slipping the earbows through the slots. Individual left and right side shields are then cut from the laminate sheet using preformed dies or other cutting techniques.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

Figure 1:
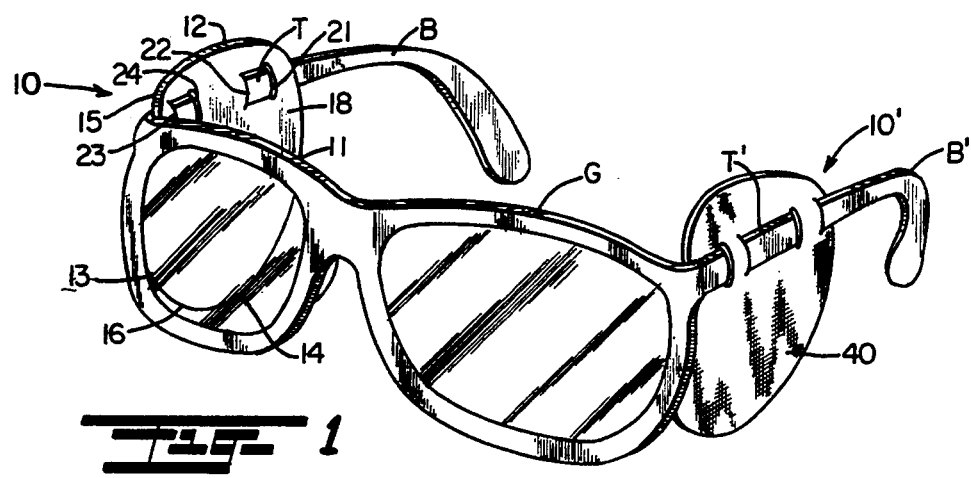
FIG. 1 is a front perspective view illustrating the side shields according to the present invention installed on a conventional pair of eyeglasses.

Referring now to the drawings, wherein like reference numerals designate corresponding structure throughout the views, and referring in particular to FIG. 1, a conventional pair of eyeglasses G, for example of the prescription or sunglass type, includes earbows B and B' having respective temple regions T and T'. A pair of side shields 10 and 10' according to the present invention are removeably secured to the temple regions T and T' of the eyeglasses G. It should be noted that the right shield 10 and the left shield 10' comprise mirror images of one another and accordingly a complete understanding of the construction of both may be had with reference to the following description of the right shield 10.

Figures 3, 4, 5:
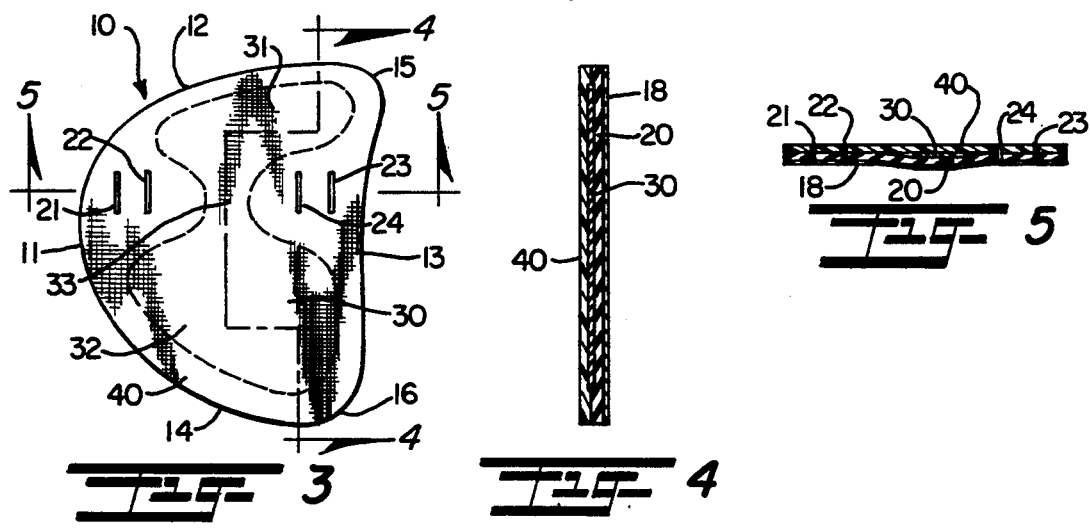
FIG. 3 is a top plan view illustrating a completed side shield according to the present invention.
FIG. 4 is a longitudinal cross-sectional view taken along line 4—4 of FIG. 3 and illustrating the internal construction of the side shield according to the present invention.
FIG. 5 is a transverse cross-sectional view taken along line 5—5 of FIG. 3 and further illustrating the internal construction of the side shield according to the present invention.

With reference to FIGS. 1 and 3, the shield 10 has a closed curve arcuate shape in a flattened condition including a first larger diameter convexly curved rear end portion 11 connected to two smaller diameter convexly curved forward corner portions 15 and 16 by two arcuate convexly curved forwardly diverging sidewalls 12 and 14. The two forward corner portions 15 and 16 are connected by a concavely curved front wall 13. Two pairs of short slits 21, 22 and 23, 24 are formed through the thickness of the shield 10 such that the earbow B of the eyeglasses G may be inserted through the slits to retain the side shield 10 in the temple region T of the earbow B to block peripheral light and wind from the right eye of a user.

Figure 2:
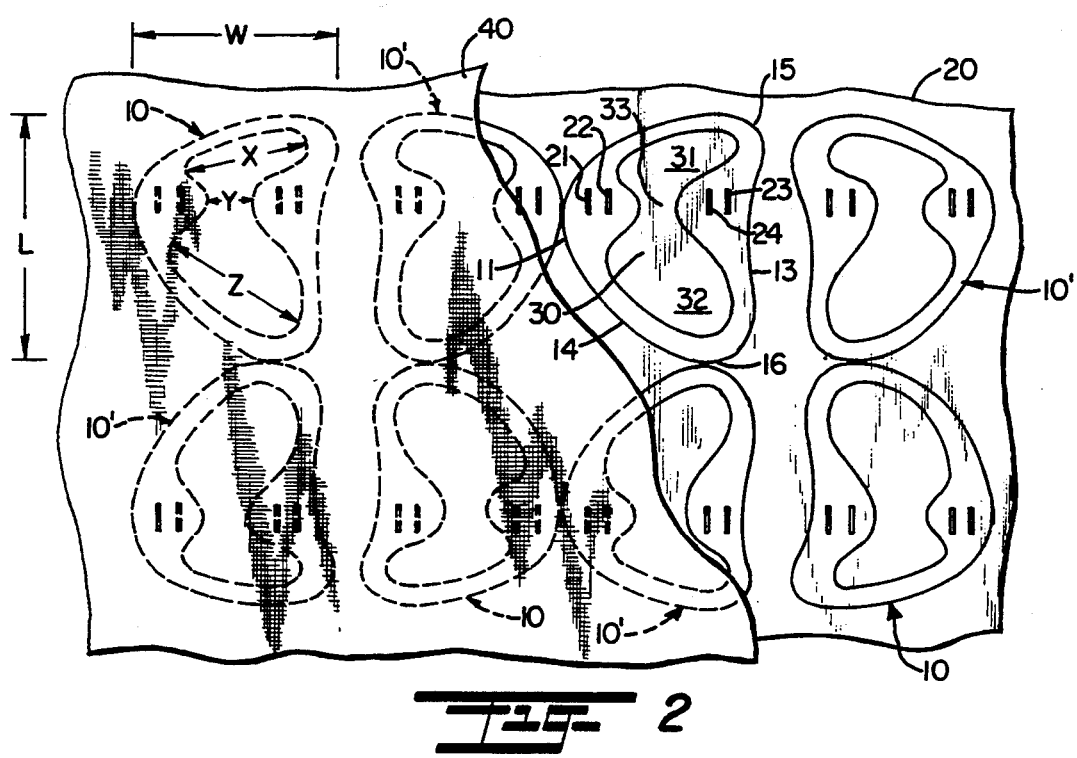
FIG. 2 is a top plan view illustrating the manner of making the side shields according to the present invention.

With reference to FIGS. 2, 4, and 5, the construction of the shields 10 and 10' will now be described in further detail. The shields 10 and 10' each include a flexible base layer comprising an inner neoprene sheet 20 laminated to an outer thin fabric sheet 18, such as a knit "LYCRA" material. The fabric sheet 18 provides a soft inner surface adapted to be disposed against the face and eyeglasses of a wearer. For the purpose of illustration but not limitation, the neoprene sheet 20 and fabric sheet 18 have thicknesses of about 0.0625 in. and 0.015 in., respectively. The base layer including the neoprene sheet 20 and laminated "LYCRA" fabric backing 18 is commercially available from Rubatex Corporation of Bedford, Va. and is of the type employed in conventional wet suits. Thus, the neoprene sheet 20 not only forms an effective barrier against wind and light, but also provides thermal insulation. Each of the shields 10 and 10' have preferred length L and width W dimensions of about 2.25 in. and 1.875 in., respectively.

A plastically deformable shape-retentive member 30 is laminated to an inner surface of the neoprene sheet 20, opposite the lycra backing 18. The shape-retentive member 30 preferably comprises a thin pliable metal foil, having a thickness less than the thickness of the base layer. Preferably, the shape-retentive member 30 comprises aluminum foil having a thickness of 0.006 in. The shape-retentive member 30 includes first and second opposite arcuate lobe ends 31 and 32, respectively, connected by a medial neck portion 33. The first lobe end 31 is substantially smaller than the second lobe end 32, and each of the lobe ends 31 and 32 are substantially larger than the medial neck portion 33. The particular shape of the shape-retentive member 30 allows the completed shield 10 and 10' to be readily deformed, while preventing any contact between the shape-retentive member 30 with either the eyeglasses or the user.

An ornamental flexible fabric cover layer 40 is laminated in overlying relation to the base layer and to the shape-retentive member 30 such that the shape-retentive member 30 is sandwiched between the base layer and the cover layer 40. The cover layer 40 may be formed with a variety of different colors and/or design patterns and has a thickness approximately that of the sheet 20.

In the manner of making the side shields 10 and 10' according to the invention, the shape-retentive members 30 are first pre-cut from a foil sheet. It should be noted that the shape-retentive members 30 for both the right shields 10 and the left shields 10' may be identically cut, and then merely flipped to the proper orientation and position on the base layer. A suitable adhesive, such as a conventional rubber cement of the type sold under the designation R27708 adhesive and thinned as required with R27123 solvent, both adhesive and solvent available from Rubatex Corporation of Bedford, Va., is then employed to laminate the shape-retentive members 30 in predetermined orientations on the neoprene sheet 20. In this regard, a suitable pattern or grid may be utilized to effect proper alignment and positioning of the shape-retentive members 30 on the base layer to minimize waste. After the shape-retentive members 30 have been glued in their proper orientations to the neoprene sheet 20, the ornamental fabric cover layer 20 is then laminated to the neoprene sheet 20 and also to the exposed upper surface of the shape-retentive members 30, again utilizing a conventional type of rubber cement.

After drying of the glue, the two pairs of short slits 21, 22 and 23, 24 are formed through the now laminated base and cover layers, with the pairs of slits disposed on opposite sides of and adjacent to the medial neck portions 33 of the shape-retentive members 30. The elastic nature of the neoprene sheet 20 allows the slits to be formed with a length suitable for a tight fit insertion of a relatively small thickness earbow, while allowing the slits to stretch sufficiently to accommodate larger thickness earbows, thus making the shields suitable for use with a wide variety of different eyeglasses. The shields 10 and 10' are then cut from the laminate sheet through the use of conventional cutting techniques, for example by die cutting or by laser cutting.

It is to be understood, however, that even though numerous characteristics and advantages of the present invention have been set forth in the foregoing description, together with details of the structure and function of the invention, the disclosure is illustrative only, and changes may be made in detail, especially in matters of materials, shape, size and arrangement of parts within the principles of the invention to the full extent indicated by the broad general meaning of the terms in which the appended claims are expressed and reasonable equivalents thereof.

I claim:

1. A side shield for eyeglasses, comprising:
a flexible base layer;
a cover layer overlying said base layer; and
a deformable shape-retentive member sandwiched between said base and cover layers, said shape-retentive member having a thickness less than a thickness of at least one of said base and cover layers.

2. The side shield of claim 1, wherein said shape-retentive member has a thickness less than a thickness of said base layer and less than a thickness of said cover layer.

3. The side shield of claim 1, wherein said shape-retentive member includes first and second opposite enlarged ends connected by a medial neck portion.

4. The side shield of claim 3, wherein said first end is smaller than said second end.

5. The side shield of claim 3, wherein each of said first and second ends are larger than said medial neck portion.

6. The side shield of claim 4, wherein each of said first and second ends are larger than said medial neck portion.

7. The side shield of claim 1, wherein said shape-retentive member comprises metal foil.

8. The side shield of claim 1, wherein said base layer comprises neoprene.

9. The side shield of claim 1, wherein said overlying base and cover layers each have a closed curve arcuate shape in a flattened condition including a first larger diameter convexly curved rear end portion connected to two smaller diameter convexly curved forward corner portions by two arcuate convexly curved forwardly diverging sidewalls, said two forward corner portions connected by a concavely curved front wall.

10. The side shield of claim 9, further comprising two pairs of short slits formed through said base and cover layers, said pairs of slits disposed on opposite sides of and adjacent to said medial neck portion, whereby an earbow of a pair of eyeglasses may be inserted through said pairs of slits to retain said side shield in a temple region of the earbow to block peripheral light and wind.

11. The side shield of claim 9, wherein said shape-retentive member includes first and second opposite ends connected by a medial neck portion.

12. The side shield of claim 11, wherein said first end is smaller than said second end.

13. The side shield of claim 11, wherein each of said first and second ends are larger than said medial neck portion.

14. The side shield of claim 9, wherein said shape-retentive member comprises metal foil.

15. The side shield of claim 1, wherein said shape-retentive member includes a reduced width medial neck portion and further comprising at least one pair of slits formed through said base and cover layers on opposite sides of said medial neck portion such that said side shield may be slipped onto a temple region of an eyeglasses earbow without direct contact between said shape-retentive member and the earbow.

16. A side shield for eyeglasses, comprising:
a flexible base layer comprising an inner neoprene sheet laminated to an outer thin fabric sheet;
a deformable shape-retentive member laminated to an inner surface of said neoprene sheet, said shape-retentive member formed from a thin metal foil having a thickness less than said base layer and having first and second opposite arcuate lobe ends connected by a medial neck portion, said first lobe end being substantially smaller than said second lobe end, and each of said first and second lobe ends being substantially larger than said medial neck portion;
an ornamental flexible fabric cover layer laminated in overlying relation to said base layer and said shape-retentive member such that said shape-retentive member is sandwiched between said base layer and said cover layer;

said overlying base and cover layers each having a closed curve arcuate shape in a flattened condition including a first larger diameter convexly curved rear end portion connected to two smaller diameter convexly curved forward corner portions by two arcuate convexly curved forwardly diverging sidewalls, said two forward corner portions connected by a concavely curved front wall; and two pairs of short slits formed through said base and cover layers, said pairs of slits disposed on opposite sides of and adjacent to said medial neck portion, whereby an earbow of a pair of eyeglasses may be inserted through said pairs of slits to retain said side shield in a temple region of the earbow to block peripheral light and wind.

17. A method of making a side shield for eyeglasses, comprising the steps of:

providing a base layer;

providing a shape-retentive member formed from a thin metal foil;

providing a cover layer; and sandwiching said shape-retentive member between said base layer and said cover layer.

18. The method of claim 17, wherein said base layer comprises neoprene.

19. The method of claim 17, further comprising the step of forming said shape-retentive member in a shape including first and second ends separated by a reduced width medial neck portion.

20. The method of claim 19, further comprising the step of forming at least one pair of slits through said base and cover layers on opposite sides of said medial neck portion.

21. The method of claim 17, wherein said base layer and said cover layer are in the form of sheets, and further comprising the steps of bonding a plurality of said shape-retentive members to a surface of one of said sheets;

laminating another of said sheets to said one sheet and to exposed confronting surfaces of said shape-retentive members; and cutting through said cover and base layers in surrounding relation to each of said shape-retentive members to form a plurality of side shields therefrom.

* * * * *